United States Patent [19]

Booher et al.

[11] Patent Number: 4,587,336

[45] Date of Patent: May 6, 1986

[54] PARTIALLY HYDROGENATED INTERMEDIATE PYRAZOLO, PYRIMIDO AND THIAZOLO[1,4]BENZOXAZINES

[75] Inventors: Richard N. Booher; Edmund C. Kornfeld, both of Indianapolis, Ind.

[73] Assignee: Eli Lilly and Company, Indianapolis, Ind.

[21] Appl. No.: 762,182

[22] Filed: Aug. 5, 1985

Related U.S. Application Data

[62] Division of Ser. No. 640,897, Aug. 15, 1984, Pat. No. 4,522,956.

[51] Int. Cl.$^4$ .............................................. C07D 265/28
[52] U.S. Cl. .................................................... 544/105
[58] Field of Search ......................................... 544/105

[56] References Cited

U.S. PATENT DOCUMENTS

| | | | |
|---|---|---|---|
| 4,198,415 | 4/1980 | Kornfeld et al. | 424/258 |
| 4,235,909 | 11/1980 | Bach et al. | 424/258 |
| 4,238,486 | 12/1980 | Jones | 424/248.4 |
| 4,318,910 | 3/1982 | Nedelec et al. | 424/248.4 |
| 4,552,956 | 11/1985 | Booher et al. | 544/101 |

OTHER PUBLICATIONS

Morrison et al., Organic Chemistry, Third Edition, Allyn and Bacon, Inc., Boston (1976) p. 456.
Hendrickson et al., Organic Chemistry, Third Edition, McGraw-Hill, New York (1970) p. 396.
Bartsch and Schwarz, J. Het. Chem., 20, 45 (1983).
Bach et al., J. Med. Chem., 23, 481 (1980).

*Primary Examiner*—Richard L. Raymond
*Attorney, Agent, or Firm*—Rowe, James L.; Arthur R. Whale

[57] ABSTRACT

Intermediates useful for the preparation of pyrazolo, pyrimido and thiazolo[1,4]benzoxazines, useful as dopamine agonists.

19 Claims, No Drawings

PARTIALLY HYDROGENATED INTERMEDIATE PYRAZOLO, PYRIMIDO AND THIAZOLO[1,4]BENZOXAZINES

This application is a division of application Ser. No. 640,897, filed Aug. 15, 1984, now U.S. Pat. No. 4,552,956, issued Nov. 12, 1985.

BACKGROUND OF THE INVENTION

The ergoline ring is a tetracycle having the following structure

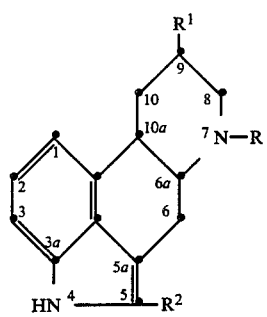

Substituted ergolines are known to be D-2 dopamine agonists having the ability to inhibit the secretion of prolactin and to affect favorably the symptoms of Parkinson's Syndrome. For example, in I when R is n-propyl, $R^1$ is methylthiomethyl, and $R^2$ is H, the substituted ergoline (as the mesylate salt) has been given the generic name pergolide—see U.S. Pat. No. 4,166,182. Pergolide is on clinical trial for the treatment of Parkinsonism and for certain conditions in which there is an excess of circulating prolactin, i.e., galactorrhea and inappropriate lactation. Another such ergoline drug is α-bromoergocryptine, named generically as bromocriptine—see U.S. Pat. Nos. 3,752,814 and 3,752,888—I when $R^2$ is Br, R is methyl and $R^1$ is the ergocryptine side chain. While both ergolines are D-2 dopamine agonists, bromocriptine, and to a lesser extent pergolide, also have some alpha blocking activity.

Ergolines are also known in which the C-10 carbon is replaced by oxygen—structure Ia below

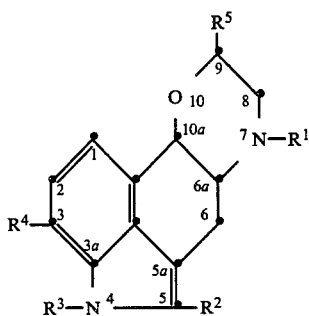

U.S. Pat. No. 4,238,486 discloses a group of such trans-dl-4,6,6a,8,9,10a-hexahydro-7H-indolo[3,4-g,h][1,4]benzoxazines, said to have antihypertensive and prolactin inhibiting properties and to be useful in treating Parkinsonism. The disclosed compounds have a benzene-ring substituent at C-3 in 15 out of 18 compounds (see Table 1) and the 5,5a double bond may be saturated. Preferred dose levels for treatment of hypertension in humans are 20–100 mg per day though daily dose levels as high as 3 g. are permitted.

U.S. Pat. No. 4,318,910 claims indolo[3,4-g,h][1,4]benzoxazines according to Ia in which $R^1$ is H but the 5,5a double bond may be hydrogenated and there may be an N-4 substituent (alkyl or aralkyl). Hypotensive, antihypertensive and rat-turning behavior (indicative of utility in treating Parkinsonism) are disclosed at doses ranging from 0.02 to 1.0 mg/kg. Daily oral dose levels in the range 0.002–1.0 mg/kg (0.15 to 75 mg per average 75 kg human per day) are advocated. The claims of the above two patents actually overlap. Only octahydro derivatives, those in which the 5,5a double bond is saturated, are claimed.

An ergoline part-structure according to formula II

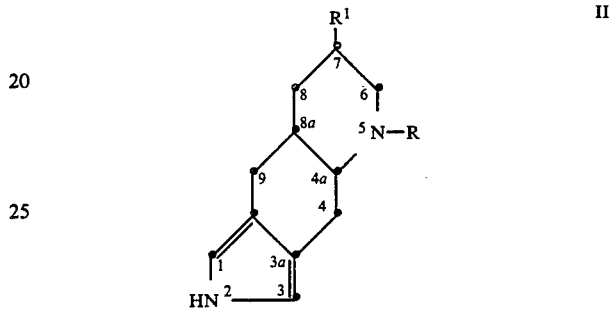

wherein R is lower alkyl, has been synthesized—see Bach et al, *J. Med. Chem.*, 23, 481 (1980), particularly structures 25 on page 483 and 34 and 35 on page 484. (See also U.S. Pat. No. 4,235,909). The compounds show activity in prolactin inhibition and rat-turning behavior tests, indicating that D-2 dopamine agonist activity is present. Related compounds in which the C-1 carbon is replaced by nitrogen to form a pyrazole ring are also disclosed by Bach et al (loc. cit.)—see compounds 38–40—in U.S. Pat. No. 4,198,415. These pyrazoloquinolines are also D-2 dopamine agonists.

Octahydropyrazolo-[4,3-g][1,4]benzoxazines hexahydro-6H-thiazolo[4,5-g][1,4]benzoxazines and hexahydro-5H-pyrimido[4,5-g][1,4]benzoxazine have not hitherto been synthesized.

DESCRIPTION OF THE INVENTION

This invention provides compounds of the formula

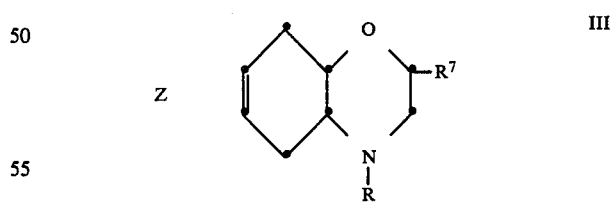

wherein Z is —HN—N=CH—, =N—NH—CH=, —N=C($NR^3R^4$)—N=CH— or —N=$CR^5$—S—; R is $C_{1-3}$ straight chain alkyl; $R^3$ and $R^4$ are individually H or R; when $R^3$ is H, $R^4$ can additionally be acetyl; $R^5$ is $NR^3R^4$, H or lower alkyl; and $R^7$ is H, $CH_2OH$, $CH_2X$, $CH_2$—Y—$C_{1-3}$ alkyl, $CH_2CN$ or $CH_2CONH_2$, wherein Y is O, S or $SO_2$, and X is a leaving group; i.e., Cl, Br, or —$OSO_2R^9$ wherein $R^9$ is lower alkyl or permissibly substituted phenyl wherein said substituents can be methyl, chloro, methoxy and the like, and pharmaceutically acceptable acid addition salts thereof. Although the stereochemistry of the ring junction is not specified in III, only those derivatives with a transfused ring junction are included within the scope of this invention, and formula III should be interpreted as covering only such trans compounds.

In one aspect, when $R^7$ is H, this invention provides trans-(±)-5-$C_{1-3}$ straight chain alkyl-1,4,4a,5,6,7,8a,9-octahydropyrazolo[3,4-g][1,4]benzoxazines (Formula IV) and the corresponding tautomers, trans-(±)-5-$C_{1-3}$ straight chain alkyl-2,4,4a,5,6,7,8a,9-octahydropyrazolo[3,4-g][1,4]benzoxazines (Formula IVa)

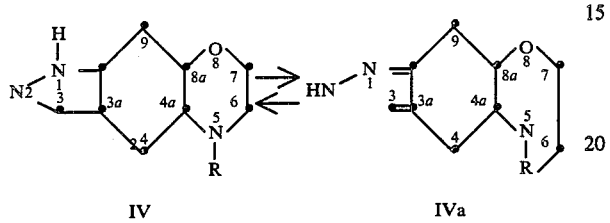

IV    IVa as well as the corresponding 4aR,8aR stereoisomeric tautomers represented by V and Va

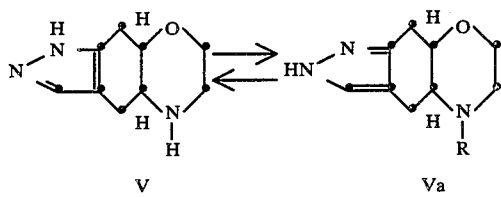

V    Va wherein R is $C_{1-3}$ straight chain alkyl, and pharmaceutically-acceptable acid addition salts thereof.

Structures IV and IVa and V and Va represent, as stated above, two tautomeric pairs; i.e., there is a dynamic equilibrium between the two members of each pair. In other words, each pyrazolo[3,4-g][1,4]benzoxazine of this invention; i.e., for example, a compound where R=n-propyl and a trans-(±) racemate is involved, cannot be represented by a single structure, but must be represented by a pair of structures such as IV and IVa. The percentages of IV and IVa or of V and Va at any given time will vary depending on the chemical environment.

In addition, the chemical compounds depicted above are a trans-(±) racemic mixture (the tautomers IV and IVa) and a 4aR,8aR isomer (the tautomers V and Va). The racemate (IV⇌IVa) can also be named as a trans-dl-5-($C_{1-3}$ straight chain alkyl)-1(or 2),4,4a,5,6,7,8a,9-octahydropyrazolo[3,4-g][1,4]benzoxazine. The 4aR,8aR tautomers (V⇌Va) can be named as a 5-($C_{1-3}$ straight chain alkyl)-1,(2),4,4aα,5,6,7,8aβ-9-octahydropyrazolo[3,4-g][1,4]benzoxazine or as a 4aR,8aR-5-($C_{1-3}$ straight chain alkyl)-1(or 2),4,4a5,6,7,8a,9-octahydropyrazolo[3,4-g][1,4]benzoxazine.

Also included within the scope of this first aspect of this invention are the trans-(±) hexahydro-5H-pyrimido[4,5-g][1,4]benzoxazines plus the corresponding 5aR,9aR enantiomers, formulas VI and VII below.

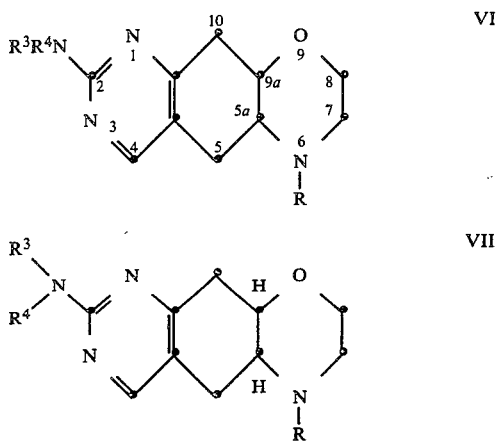

wherein R has its previous meaning and $R^3$ and $R^4$ are individually H or R and when $R^3$ is H, $R^4$ can additionally be acetyl. The above compounds are named as follows: VI, a racemate, is a trans-(±)-6-($C_{1-3}$ straight chain alkyl)-5a,6,7,8,9a,10-hexahydro-5H-pyrimido[4,5-g][1,4]benzoxazine and VII is a 5aR,9aR-6-($C_{1-3}$ straight chain alkyl)-5a,6,7,8,9a,10-hexahydro-5H-pyrimido[4,5-g][1,4]benzoxazine. The compounds represented by VI and VII are also D-2 dopamine agonists.

Another group of D-2 dopamine agonists and another part of the first aspect of this invention are compounds having structural features in common with IV, Va, V, Va, VI and VII, but containing a different aromatic heterocyclic ring. These novel compounds are the racemic hexahydro-6H-thiazolo[4,5-g][1,4]benzoxazines of formula VIII, and the 4aR,8aR stereoisomers of formula IX

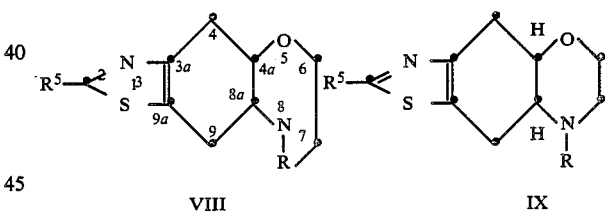

VIII    IX where $R^5$ is H, lower alkyl or $NR^3R^4$; $R^3$ and $R^4$ are H or R; or when $R^3$ is H, $R^4$ can in addition be acetyl.

Racemates according to VIII are named as trans-(±)(or trans-dl)-8-($C_{1-3}$ straight chain alkyl)-4,4a,7,8-,8a,9-hexahydro-6H-thiazolo[4,5-g][1,4]benzoxazines and the stereoisomer IX is named as a 4aR,8aR-8-($C_{1-3}$ straight chain alkyl)-4,4a,7,8,8a,9-hexahydro-6H-thiazolo[4,5-g][1,4]benzoxazines.

Structures according to IV⇌IVa, V⇌Va, VI, VII, VIII, and IX have two asymmetric carbons, those at the ends of the benzoxazine ring bridgehead. Thus, compounds of that basic structure exist as two racemates, the trans-(±) racemate, the one actually specified by the formula and provided by this invention, and a cis-(±) racemate. The synthetic procedures which follow produce mainly the trans-(±) racemates in detectable quantities—see reaction Scheme I below —XVI→XVIIa+XVIIb via NaBH₄.

The above compounds also contain at least two basic nitrogens, one the alkylated[1,4]benzoxazine ring nitrogen and the other a heterocyclic ring nitrogen in the ring fused to the benzoxazine. The hydrogenated benzoxazine ring nitrogen is the more basic of the two and forms acid addition salts readily. Strong inorganic acids such as the mineral acids or strong organic acids, such as p-toluenesulfonic acid, can form di salts when employed in excess with the compounds of this invention.

In structures VI and VII and in VIII and IX, when $R^5$ is neither H nor lower alkyl, there is a third basic group present, the $NR^3R^4$ group. The basicity of this group varies depending on the nature of $R^3$ and $R^4$; ie, from weakly basic when $R^3$ is H and $R^4$ is H or acetyl, to strongly basic when $R^3$ and $R^4$ are both alkyl. Thus, trisalts are possible and disalts are readily prepared when $NR^3R^4$ is a strongly basic group. Pharmaceutically-acceptable acid addition salts of the compounds of this invention include mono, di or tri salts derived from inorganic acids such as: hydrochloric acid, nitric acid, phosphoric acid, sulfuric acid, hydrobromic acid, hydriodic acid, phosphorous acid and the like, as well as salts derived from organic acids such as aliphatic mono and dicarboxylic acids, phenyl-substituted alkanoic acids, hydroxyalkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihyrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, α-hydroxybutyrate, glycollate, malate, tartrate, methanesulfonate, propanesulfonate, naphthalene-1-sulfonate, naphthalene-2-sulfonate and the like salts.

The compounds of this invention are all synthesized from a bicyclic ketone starting material prepared according to the following reaction scheme:

Reaction Scheme I

-continued
Reaction Scheme I

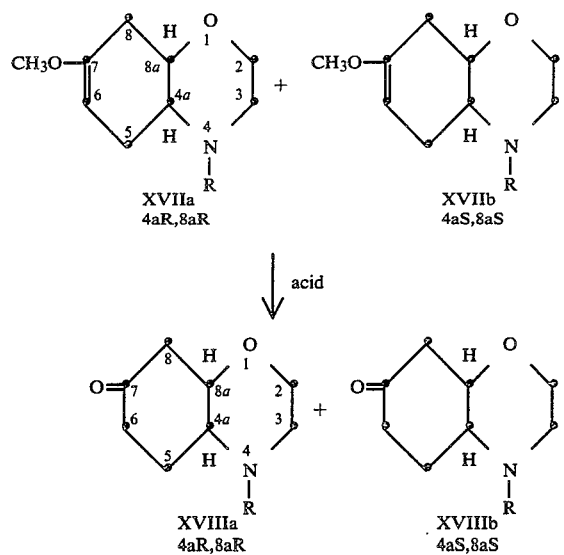

wherein R has its previous meaning. In the above procedure, the products XVIIa and XVIIb and XVIIIa and XVIIIb occur in each case as a trans racemate in which the two stereoisomers depicted are present in equal quantities.

According to Reaction Scheme I, 2,4-dimethoxyaniline (X) is acylated with chloroacetylchloride in the presence of an organic or inorganic base, triethylamine being a convenient choice, to yield the N-chloroacetyl derivative (XI). Next, the N-(chloro)acetanilide (XI) is selectively demethylated with $AlCl_3$ or $BBr_3$ in a mutual nonreacting solvent such as $CH_2Cl_2$ to yield XII. The free hydroxyl of XII then cyclizes readily with the activated chlorine of the chloroacetyl side chain in the presence of base to yield the internal ether, 3-oxo-7-methoxy-3,4-dihydro-2H-[1,4]benzoxazine (XIII). The nitrogen of the benzoxazine ring is then alkylated, as with a $C_{1-3}$ straight chain alkyl halide—RX— in the presence again of base, to yield XIV. The 3-oxo group is next removed by $BH_3$ reduction in a suitable solvent such as THF (tetrahydrofuran). This derivative XV—an N-alkyl-7-methoxydihydro-2H-[1,4]benzoxazine, is next subjected to a Birch reduction (Li in liquid $NH_3$). The product is a 4-$C_{1-3}$ straight chain alkyl-3,4,5,8-tetrahydro-2H-[1,4]benzoxazine XVI. Stereospecific reduction of this eneamine with a metal hydride ($NaBH_4$, $NaCNBH_3$) in THF or other suitable solvent in the presence of acid (acetic acid is a convenient choice) yields trans-(±)-4-($C_{1-3}$ straight chain alkyl)-7-methoxy-3,4,4a,5,8,8a-hexahydro-2H-[1,4]benzoxazine (XVIIa and XVIIb represent the two stereoisomers constituting the racemate). The reduction step XVI to the racemic pair XVIIa and XVIIb is stereospecific in that only the trans racemate is isolated. The cis racemate is present, if at all, in amounts that are non-detectable by ordinary chemical methods. Treatment of the racemate XVIIa and XVIIb with acid de-enolizes the 7-enolethers to form the desired racemic ketone, XVIIIa (4aR,8aR) and XVIIIb (4aS,8aS). The racemate can be resolved by adapting the procedures of Schaus and Booher, Ser. No. 439,107 filed Nov. 3, 1982, to yield the individual enantiomeric ketones.

Alternatively, the intermediate XIV where R is $CH_3$, $C_2H_5$ or n-$C_3H_7$ ($CH_2R^6$ where $R^6$ is H, CH, or $C_2H_5$) can be prepared according to Reaction Scheme II below.

Reaction Scheme II

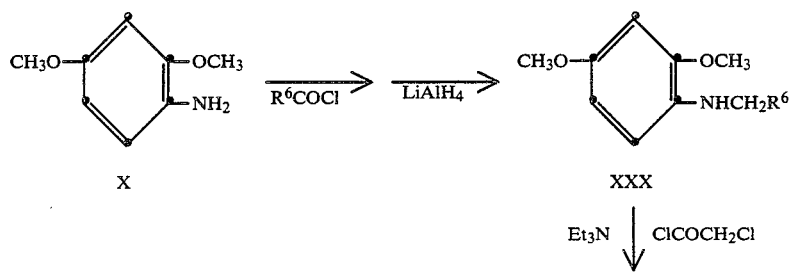

-continued

Reaction Scheme II

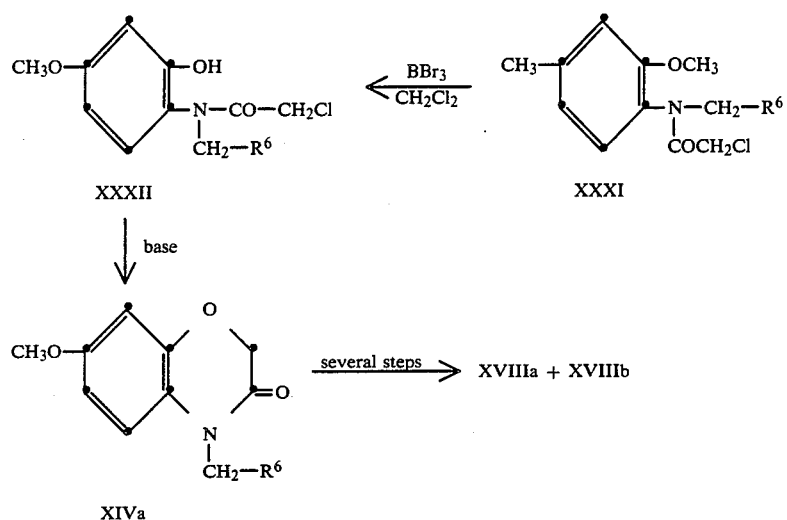

wherein $R^6$ is H, $CH_3$ or $C_2H_5$.

Alkylation of X with an alkyl iodide and strong base rather than by acylation followed by LiAlH₄ reduction, also yields XXX and, eventually, compounds of the formula

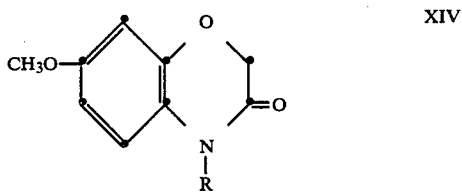

Conversion of the intermediate trans racemate (XVIII) or 4aR,8aR (XVIIIa) or 4aS,8aS (XVIIIb) enantiomers to the products of this invention according to formulas IV⇌IVa, VI and VIII above is set forth in Reaction Scheme III below.

Reaction Scheme III

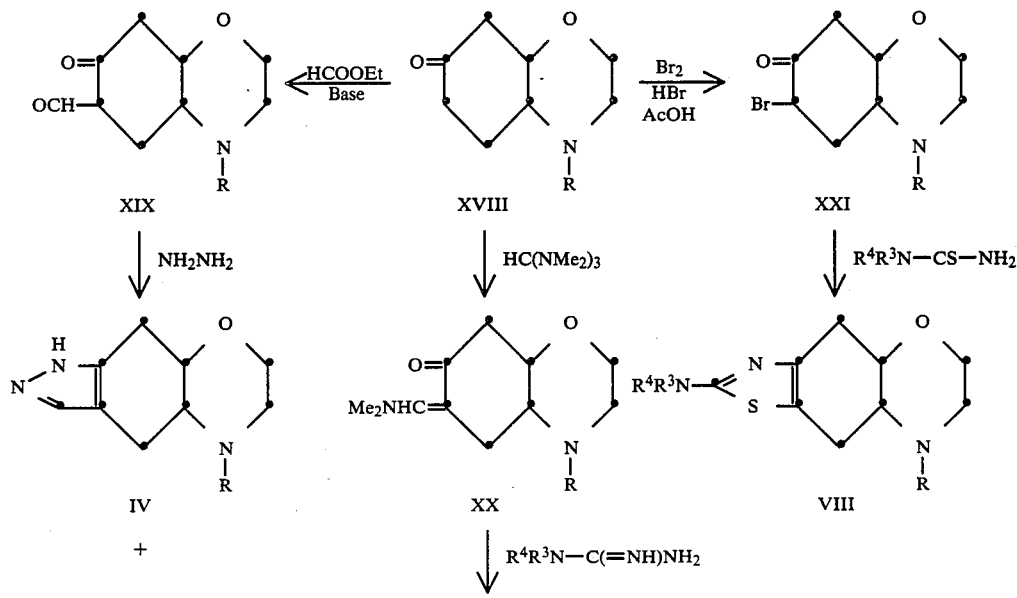

-continued
Reaction Scheme III

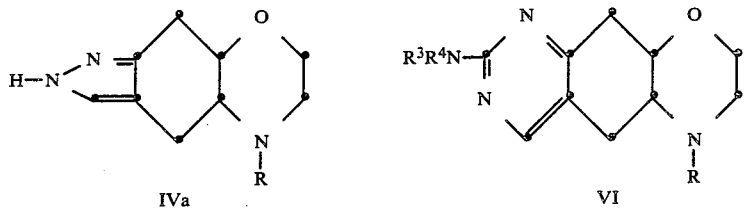

IVa  VI wherein R, $R^3$ and $R^4$ have their previous meanings. Compounds according to VIII or IX wherein $R^5$ is H are prepared by diazotizing VIIIb where $R^3$ and $R^4$ are both H and then treating the diazonium salt with hypophosphorous acid or the like.

In Reaction Scheme III above, the 7-formyl derivative XIX has been written as a single structure. By analogy with the corresponding trans-($\pm$)-1-alkyl-6-oxo-7-formyldecahydroquinoline of Schaus, Ser. No. 438,834 filed Nov. 3, 1982, the intermediate XIX is better represented as a series of tautomers (XIXa to XIXd) below

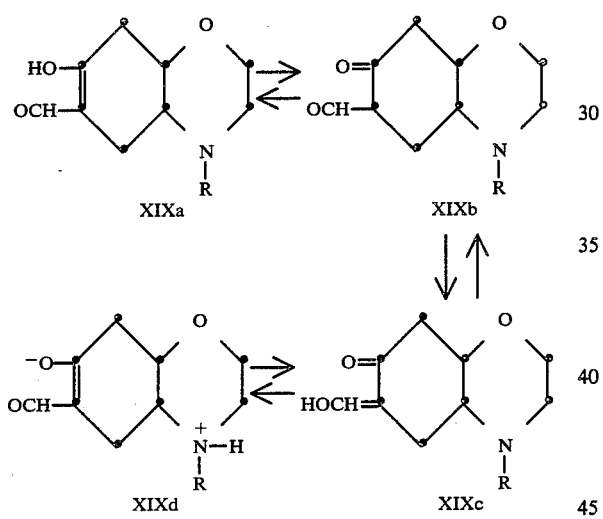

XIXa  XIXb

XIXd  XIXc

In Reaction Scheme III and in the examples which follow, a trans-($\pm$) racemate is indicated by a lack of a specific orientation for the 4a and 8a hydrogens in the starting material. Obviously, by substituting a 4aR,8aR-1-$C_{1-3}$ straight chain alkyl-7-oxo-octahydroquinoline or the 4aS,8aS enantiomer for the trans-($\pm$) racemate, the corresponding 4aR,8aR or 4aS, 8aS-enantiomers of IV⇌IVa, or VIII and the 5aR,9aR or 5aS,9aS enantiomers of VI would be prepared. These enantiomers of V, VII and IX above are D-2 dopamine agonists, and, in general, the trans ($\pm$) racemates are useful as D-2 agonists because of their content of 4aR,8aR or 5aR,9aR enantiomer. The 4aS,8aS or 5aS,9aS enantiomers, the other components of the given racemates, are D-1 agonists. The presence of the D-2 agonistic enantiomers in the racemate, however, overpowers any D-1 activity of the trans-($\pm$) racemates.

In a second aspect of this invention, there are provided useful intermediates and final products in which $R^7$ in III above is other than H. Those compounds have the following structure LX

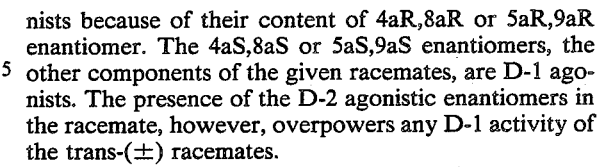

wherein Z is $-HN-N=CH-$, $-N=C(NR^3R^4)-N=CH$ or $-N=CR^5-S-$, R is $C_{1-3}$ straight chain alkyl, $R^3$ and $R^4$ are individually R or H, $R^5$ is H, lower alkyl or $NR^3R^4$, wherein, when $R^3$ is H, $R^4$ can also be acetyl, and $R^7$ is $CH_2OH$, $CH_2X$, $CH_2-Y-C_{1-3}$alkyl, $CH_2CN$ or $CH_2CONH_2$ wherein Y is O, S or $SO_2$, and X is a leaving group; ie, Cl, Br, or $-OSO_2R^9$ wherein $R^9$ is lower alkyl or permissibly substituted phenyl wherein said substituents are methyl, chloro, methoxy and the like, and pharmaceutically acceptable acid addition salts thereof. Although the stereochemistry of the ring function is not specified, only the trans derivatives are included within the scope of formula LX.

In formula LX above, when Z is $-HN-N=CH$, the resulting compound is one tautomer of an octahydropyrazolo[3,4-g][1,4]benzoxazine of structure LXI. As before, when one tautomer is named, the other tautomer is implied.

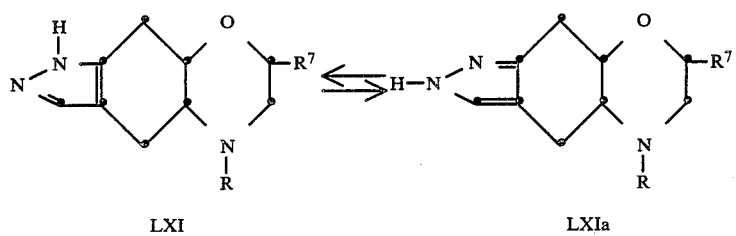

LXI  LXIa wherein R has its previous meaning.

In LX above, when Z is $N=C(NR^3R^4)-N=CH-$, a trans hexahydro-5H-pyrimido[4,5-g][1,4]benzoxazine of structure LXII is described

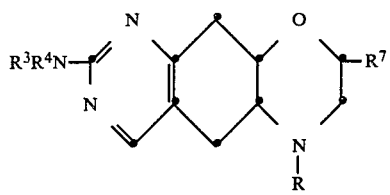
LXII wherein R, $R^3$ and $R^4$ have their previous meaning. When Z is

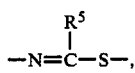

a trans hexahydro-6H-thiazolo[4,5-g][1,4]benzoxazine of formula LXIII is described

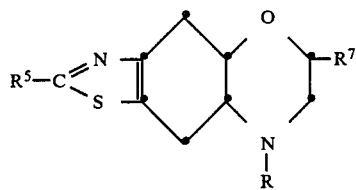
LXIII wherein R and $R^5$ have their previous meaning.

The pharmaceutically-acceptable acid addition salts of the above compounds are the same as those given above for compounds in which $R^7$ is H. Compounds in which $R^7$ is $CH_2OH$ or $CH_2X$ are intermediates whereas compounds where $R^7$ is $CH_2CN$, $CONH_2$ or $CH_2$—Y—$C_{1-3}$alkyl are final products, active as dopamine agonists.

The above compounds (LX etc.) are synthesized from a bicyclic ketone intermediate, which intermediate is prepared according to Reaction Scheme IV below.

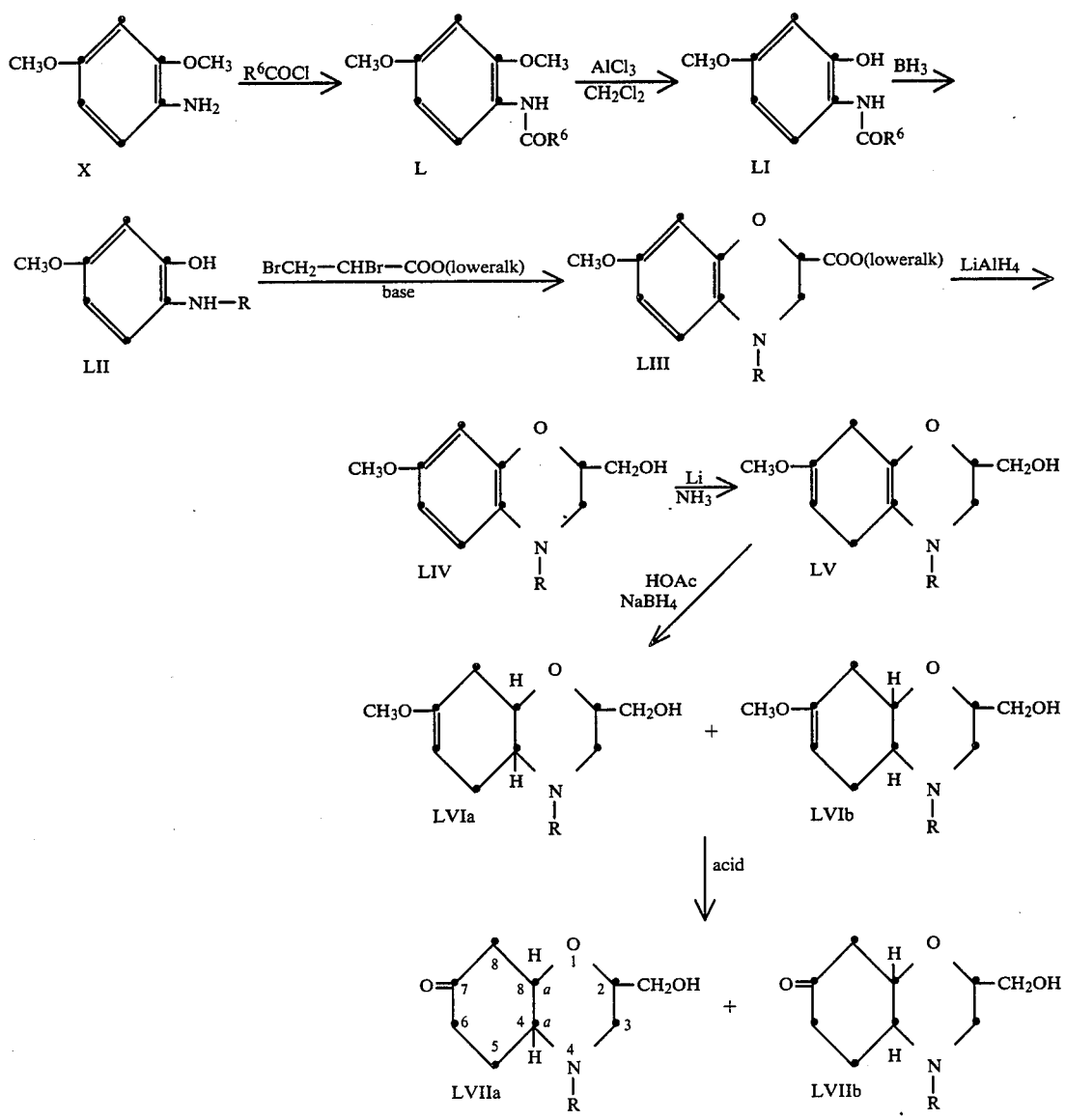

wherein $R^6$ is H, $CH_3$, $C_2H_5$ and R has its previous meaning; i.e., is $C_{1-3}$ straight chain alkyl.

In the above reaction scheme, 2,4-dimethoxyaniline (X) is also used as a starting material as it was in Reaction Scheme I. However, the N—$C_{1-3}$ straight chain alkyl substituent is placed on the "eventual" oxazine ring nitrogen prior to the ring closure reaction. An N-acylation is first carried out conveniently with an alkanoylhalide, $R^6COCl$; ie., formylchloride, acetylchloride or n-propionylchloride to give an N-acyl derivative, L. The N-acyl-2,4-dimethoxyaniline is then demethylated as in Reaction Scheme I; i.e., the ortho methoxyether is cleaved to the ortho hydroxy derivative, LI. Next, the N-acyl group is reduced with $BH_3$ is a suitable inert solvent to yield the N—$C_{1-3}$ straight-chain alkyl derivative, LII. Reaction of a 1,2-dibromopropionate ester in the presence of a suitable base with LII yields the oxazine LIII, a 4-$C_{1-3}$ straight chain alkyl-7-methoxy-3,4-dihydro-2H-[1,4]benzoxazinyl-2-carboxylic acid ester. Next, the ester group is reduced with $LiAlH_4$ to an hydroxymethylene group (LIV). This 2-hydroxymethyl-4-alkyl-7-methoxydihydro-2H-[1,4]benzoxazine is then subjected to a Birch reduction to yield the tetrahydro-2H-benzoxazine (LV) followed by a stereoselective reduction of the thus-formed enamine to yield two stereoisomers of 7-methoxyhexahydro-2H-[1,4]benzoxazine (the 4aR,8aR and 4aS,8aS isomers are represented by LVIa and LVIb). An acidic hydrolysis of the enol ether (LVIa and LVIb) yields the trans-($\pm$)-2-hydroxymethyl-4-$C_{1-3}$ straight chain alkyl-7-oxo-3,4,4a,5,6,7,8,8a-octahydro-2H-[1,4]benzoxazine (LVIIa and LVIIb) stereoisomers.

At this point, after separating the stereoisomers, alternative paths are available for production of D-2 or D-1 agonists of structure LX wherein R is $C_{1-3}$ straight chain alkyl and $R^7$ is $CH_2CN$ or $CH_2$—Y—$C_{1-3}$ alkyl where Y is S, O or $SO_2$. As a first step, the hydroxyl of the C-2 hydroxymethyl group is replaced with a "leaving group"; i.e., a group readily displaced by a nucleophilic reagent, such leaving groups including chlorine, bromine and the halogen-like esters, tosylate (usually p-toluene sulfonate), alkyl sulfonate, benzene sulfonate etc., to produce a compound wherein $R^7$ is $CH_2X$ and X has its previous meaning. The Cl or Br leaving groups are introduced by reaction with $PCl_3$, $SOCl_2$, $PCl_5$, $POCl_3$, $PBr_3$ and the like, and the sulfonate esters by reaction of the alcohol with the corresponding sulfonyl chloride. Reaction of a compound wherein $R^7$ is $CH_2X$ and X is a leaving group with sodium methylate, methylmercaptan sodium salt, sodium cyanide, sodium methanesulfinate or other basic salts of methanol, methylmercaptan etc. yields trans($\pm$) racemates of the formula

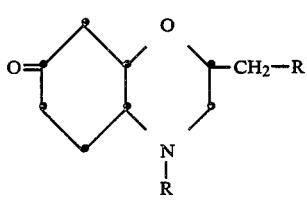

LVIII wherein R is methyl, ethyl or n-propyl and $R^{12}$ is CN, $CONH_2$ or —Y—$C_{1-3}$ alkyl where Y is O, S or $SO_2$. This intermediate, or an enantiomer thereof produced by resolution of the racemate LVIII, can then be formylated or brominated ortho to the ring ketone and that intermediate reacted with hydrazine, guanidine, thiourea, an amino-substituted guanidine or an amino-substituted thiourea in accordance with Reaction Scheme III to produce those drugs represented by LX when $R^7$ is $CH_2R^{12}$.

Alternatively, the intermediate 2-hydroxymethyl derivative (LVIIa or LVIIb) can be transformed into a compound of structure LX wherein $R^7$ is $CH_2OH$. The hydroxymethyl group can then be replaced with a leaving group ($R^7$ is $CH_2X$) and the leaving group replaced with cyano, carboxamido, lower alkyl mercapto, lower alkyloxy or lower alkyl sulfinyl to yield the desired D-1 and/or D-2 agonists. However, there is one caveat to this second reaction scheme. In reacting a pyrazole, aminopyrimidine or aminothiazole where the amine group is primary or secondary, a sulfonyl halide will react with both that amine group and the hydroxymethyl group. Thus, two moles of sulfonyl halide should be used per mole of octahydro-2H-[1,4]benzoxazine and the intermediate will, at least in part, be a disulfonate. In the next step of the reaction, however—replacement of the group X in $CH_2X$ with Y—$C_{1-3}$ alkyl etc.—the basic conditions utilized serve not only to effect replacement of the leaving group, but also to remove the second sulfonyl group in the hetero (pyrazole, thiazole, pyrimidine) ring.

Alternatively, the same series of reactions can be carried out on the intermediate racemic trans-($\pm$)-2-hydroxymethyl-7-oxo-octahydro-2H-[1,4]benzoxazine or one of its enantiomers (LVIIa and b). As a first step, however, the 7-oxo group must be protected, as by ketal formation with ethyleneglycol. Again alternatively, the 2-hydroxymethyl enol ether intermediate (LVIa and LVIb) can be used as the starting material. In either instance, the 2-hydroxymethyl group is esterified with a sulfonyl halide or the hydroxyl replaced with halogen to prepare a 2-$CH_2X$ derivative where X is a leaving group. As above, reaction with sodium methylate, the sodium salt or methyl mercaptan or the other sodium salt, yields derivatives in which $R^7$ is $CH_2$—S—$CH_3$, $CH_2$—O—$CH_3$, $CH_2CN$, $CH_2SO_2CH_3$ or the like side chain. Such a derivative can then be treated with acid to convert the 7-enol ether or 7-ketal to a 7-keto derivative. This 7-keto compound can then serve as a starting material to prepare the D-1 and D-2 agonists of this invention, using the synthetic step of Reaction Scheme II to prepare active drugs according to LX (LXI, LXIa, LXII and LXIII) in which $R^7$ is $CH_2CN$, $CH_2$—Y—$C_{1-3}$ straight chain alkyl where Y is S, $SO_2$ or O. Compounds wherein $R^7$ is $CH_2CONH_2$ are prepared by an alkaline hydrolysis of the corresponding compound in which $R^7$ is $CH_2CN$.

Compounds according to LVIa, LVIb, LVIIa, LVIIb, LX, LVIII, LXI⇌LXa, LXII and LXIII have three optical centers, two at the bridgehead (4a,8a or 5a,9a carbons depending on which structure is involved) and a third center ortho to the oxazine ring oxygen, the carbon carrying the $R^7$ substituent. The $R^7$ substituent thus can have either an $\alpha$ or a $\beta$ configuration. As with the derivatives lacking the $R^7$ substituent, only the trans-diastereoisomers (referring to the configuration of the ring junction carbons) are isolateable after the borohydride reduction (Reaction Scheme I—XVII to XVIIa and XVIIb; Reaction Scheme IV—LIV to LVa and LVb). This stereoselective step, yielding mainly derivatives with a trans ring-fusion, decreases by half the number of expected diastereoisomers. Thus, although there are three asymmetric carbons and the expected number of stereoisomers is $n^3=8$, only four stereoisomers are actually found, existing as two racemates, conveniently designated as the α-trans-(±) and β-trans-(±) racemates. Both such racemates and the individual stereoisomers composing these racemates are included within the scope of this invention.

Derivatives of V⇌Va, VII and IX and the racemates containing these stereoisomers constitute a preferred aspect of this invention.

This invention is further illustrated by the following specific examples.

EXAMPLE 1

Preparation of Trans-(±)-4-n-propyl-3,4,4a,5,6,7,8,8a-octahydro-2H-[1,4]benzoxazin-7-one A solution was prepared from 15.3 g of 2,4-dimethoxyaniline and 10.1 g of triethylamine in 300 ml of methylenedichloride. The solution was cooled to about 0° C. Eleven and three tenths grams of chloroacetylchloride were added in dropwise fashion with stirring under a nitrogen blanket. After the addition had been completed, the reaction mixture was stirred at ambient temperature for 1 hour. The reaction mixture was then extracted successively with equal volumes of 1N hydrochloric acid and of water. The organic solution was next extracted with cold saturated aqueous sodium bicarbonate followed by a second extraction with water. All these aqueous extracts were discarded. The organic solution was dried, and the solvent removed in vacuo. A residue consisting of 23 g of a purple colored solid was obtained. Twenty-one grams of this residue were chromatographed over silica gel using ethyl acetate as the eluant in order to remove a colored impurity. Fractions containing the desired product, N-chloroacetyl-2,4-dimethoxyaniline were combined and the solvent removed therefrom to yield a tan solid residue. Recrystallization of the residue from an ethyl acetate/hexane solvent mixture gave 16.5 g of N-chloroacetyl-2,4-dimethoxyaniline melting at 90°–91° C. (yield=72%).

Analysis. Calc.: C, 52.30; H, 5.27; N, 6.10. Found: C, 52.50; H, 5.25; N, 6.07.

A solution was prepared from 2.28 g of N-chloroacetyl-2,4-dimethoxyaniline and 100 ml of methylenedichloride. The solution was cooled to about −78° C. 2.51 g of boron tribromide were added in dropwise fashion with stirring. The reaction mixture was cooled at −78° C. for an additional 30 minutes and was then allowed to warm to ambient temperature over a 2 hour period. 50% aqueous ethanol was added, and the resulting mixture refluxed for 2 hours. The ethanol was removed in vacuo, and the aqueous fraction extracted twice with equal volumes of methylenedichloride. The methylenedichloride extracts were combined, and the combined extracts washed with water and then dried. Removal of the solvent in vacuo gave 2 g of a tan solid comprising N-chloroacetyl-2-hydroxy-4-methoxyaniline formed in the above demethylation reaction. TLC (50% ethyl acetate/benzene) showed a small amount of an impurity and a slower moving major product. The tan solid was therefore recrystallized from ethyl acetate/hexane to yield crystalline material melting at about 161°-2° C.; yield=100 mg.

Analysis. Calc.: C, 50.13; H, 4.67; N, 6.50; Cl, 16.44; Found: C, 49.84; H, 4.43; N, 6.21; Cl, 16.28.

The above reaction was repeated except that three equivalents of aluminum chloride were added in place of BBr₃, and the demethylation mixture was stirred overnight at ambient temperature. An 82% yield of the desired N-chloroacetyl-2-hydroxy-4-methoxyaniline was obtained in this second run.

A reaction mixture was prepared from 19.6 g of N-chloroacetyl-2-hydroxy-4-methoxyaniline, 13.8 g of potassium carbonate and 500 ml of acetone. The mixture was refluxed with stirring for about 5 hours and was then cooled. Inorganic salts were separated by filtration, and the solvent removed from the filtrate in vacuo. The resulting residue was dissolved in methylenedichloride. The methylenedichloride solution was washed with saturated aqueous sodium chloride and then dried. Fourteen grams of 3,4-dihydro-7-methoxy-2H-[1,4]benzoxazin-3-one were obtained. NMR indicated complete cyclization to the lactam. Recrystallization from ethyl acetate/hexane yielded product melting at 164°–165° C.

Analysis. Calc.: C, 60.33; H, 5.06; N, 7.82; Found: C, 60.11; H, 5.13; N, 7.86.

A reaction mixture was prepared from 14 g of 3,4-dihydro-7-methoxy-2H-[1,4]benzoxazin-3-one, 17 g of n-propyl iodide, 13.8 g of potassium carbonate and 500 ml of acetone. The reaction mixture was refluxed overnight with stirring and was then cooled. An additional 17.0 g of n-propyl iodide and 13.8 g of potassium carbonate were added. The reaction mixture was then refluxed for an additional 48 hours, after which time it was cooled and any inorganic salts therein removed by filtration. The solvent was removed from the filtrate in vacuo, and the residue, comprising 3,4-dihydro-7-methoxy-4-n-propyl-2H-[1,4]benzoxazin-3-one obtained in the above reaction, was taken up in a mixture of water and methylenedichloride. The organic layer was separated, and the solvent removed therefrom in vacuo. 15.5 g of an oil, comprising 4-n-propyl-7-methoxy-3,4-dihydro-2H-[1,4]-benzoxazin-3-one were obtained.

A reaction mixture was prepared by adding, in dropwise fashion, 15.5 g of 4-n-propyl-7-methoxy-3,4-dihydro-2H-[1,4]benzoxazin-3-one in 100 ml of THF to 150 ml of a 1M BH₃ solution in THF at 0° C. The reaction mixture was stirred for 2 hours at reflux temperature. 150 ml. of 6N HCl were added to decompose any excess BH₃. The reaction mixture was concentrated in vacuo, and the resulting acidic solution was warmed at about 100° C. The acidic solution was then extracted with ethyl acetate. The ethyl acetate layer was separated and discarded. The acidic aqueous layer was made basic, and the base-insoluble oxazine extracted into ethyl acetate. The organic layer was washed with water and with brine and was then dried. The solvents were removed therefrom in vacuo. The residue, weight=13 g., was distilled; B.P.=115°–120° C. at 0.05 torr; yield=12 g of 4-n-propyl-7-methoxy-3,4-dihydro-2H-[1,4]benzoxazine.

Ammonia was dried by passage through a barium oxide drying tower. 100 ml. of ammonia thus dried were condensed in a cooled (below −33° C.) 500 ml round bottom flask equipped with Dewar condenser (containing a dry ice/acetone mixture) and a magnetic stirrer. 1.53 g of lithium (taken from a lithium rod and the rod cut into small pieces) was added to the liquid ammonia over a 15 minute period. A deep blue color appeared. After all of the lithium metal had been added, the solution was stirred for about 30 minutes. Next, a solution of 7 g of 4-n-propyl-7-methoxy-3,4-dihydro-2H-[1,4]benzoxazine in 25 ml of THF was added in dropwise fashion to the solution of lithium in liquid ammonia. After the addition had been completed, the reaction mixture was stirred for an additional 30 minutes, at which time 34 ml of anhydrous ethanol were added. The condenser was removed, and gaseous nitrogen blown through the reaction mixture to remove excess ammonia. 100 ml of water were added to the residual colorless solution. An initial white precipitate which formed redissolved as more water was added. The aqueous mixture was extracted several times with equal volumes of methylenedichloride. The combined methylenedichloride extracts were washed with brine and then dried. The solvent was removed in vacuo to yield 6 g of an oil containing, as a major product, the enamine, 4-n-propyl-7-methoxy-3,4,5,8-tetrahydro-2H-[1,4]benzoxazine formed in the above reduction.

A solution was prepared by dissolving 18 g of the above enamine in 150 ml of methanol. The solution was placed in a 3-necked round bottom flask under a nitrogen atmosphere. 5.14 ml of glacial acetic acid were added followed by a solution of 3.78 g of sodium borohydride in 150 ml of anhydrous ethanol. The borohydride solution was added in dropwise fashion with stirring over a 15 minute period. The reaction mixture was stirred at ambient temperature for about 2 hours. Ten ml of 6N hydrochloric acid were added to lower the pH of the reaction to about 1.5. This new mixture was stirred for an additional hour. The solution was filtered, and the filtrate concentrated in vacuo to an oily residue. The residue was dissolved in water, and 50% aqueous sodium hydroxide was added until the pH of the aqueous layer was in the range 10–11. The now-basic mixture was extracted twice with methylenedichloride. The methylenedichloride extracts were combined, and the combined extracts washed with brine and then dried. Removal of the solvent in vacuo yielded 14 g of a dark red oil. The oil was dissolved in methylenedichloride, and a solution of 15.6 g of sodium bisulfite in 60 ml of water was added to the methylenedichloride solution in dropwise fashion with stirring under a nitrogen atmosphere. Stirring was continued overnight at room temperature. Additional water and methylenedichloride were added, and the methylenedichloride layer separated. The aqueous layer was made basic by the addition of 50% aqueous sodium hydroxide. The basic layer was then extracted three times with equal volumes of methylenedichloride. The methylenedichloride extracts were combined, and the solution washed twice with brine and then dried. Removal of the solvent in vacuo yielded a 9.2 g (58% yield) of a lightly colored oil comprising trans-($\pm$)-4-n-propyl-3,4,4a,5,6,7,8,8a-octahydro-2H-[1,4]benzoxazin-7-one formed in the above reaction, having a molecular ion at 197 by mass spectrum. NMR was consistent with the postulated structure.

EXAMPLE 2

Preparation of Trans-($\pm$)-4-methyl-3,4,4a,5,6,7,8,8a-octahydro-2H-[1,4]benzoxazin-7-one Following the procedure of Example 1, 21.7 g of 3-oxo-7-methoxy-3,4-dihydro-2H-[1,4]benzoxazine and 19.88 g of methyl iodide were reacted in 600 ml of acetone in the presence of 19.32 g of solid potassium carbonate. The reaction was carried out, and the product isolated and purified by the procedure of Example 1 to yield 3-oxo-4-methyl-7-methoxy-3,4-dihydro-2H-[1,4]benzoxazine; yield=92%; molecular ion by mass spectrum=193.

Still following the procedure of Example 1, 21 g of 4-methyl-7-methoxy-3,4-dihydro-2H-[1,4]benzoxazin-3-one were reduced with 1M BH$_3$ in THF solution. The reaction was carried out and the product isolated by the procedure of Example 1 to yield 4-methyl-7-methoxy-3,4-dihydro-2H-[1,4]benzoxazine; B.P.=105° C. at 0.025 torr; yield=16 g. Following the procedure of Example 1, 16 g of the above 4-methyl-7-methoxy-2H-[1,4]benzoxazine was subjected to a Birch reduction with lithium metal in anhydrous ammonia as follows: the oxazine was dissolved in 75 ml of THF and the solution added to a solution of 4.42 g of lithium metal dissolved in 300 ml of anhydrous ammonia. 100 ml of anhydrous ethanol were added during the course of the reaction. The product, 4-methyl-7-methoxy-3,4,5,8-tetrahydro-2H-[1,4]benzoaxazine, weighed 15.2 g.

Following the procedure of Example 1, 15.2 g of the above enamine in 150 ml of methanol were reduced with 3.78 g of sodium borohydride in 150 ml of ethanol in the presence of 5.14 ml of glacial acetic acid. The product of the reaction, trans-($\pm$)-4-methyl-7-methoxy-3,4,4a,5,8,8a-hexahydro-2H-[1,4]benzoxazine, was hydrolysed by treatment with acid as in Example 1 to yield trans-($\pm$)-4-methyl-3,4,4a,5,6,7,8,8a-octahydro-2H-[1,4]benzoxazin-7-one. The product was purified from a highly colored impurity by treatment with sodium bisulfite as in Example 1.

EXAMPLE 3

Preparation of Trans-($\pm$)-5-n-propyl-1(or 2),4,4a,5,6,7,8a,9-octahydropyrazolo[3,4-g][1,4]benzoxazine and of Trans-($\pm$)-5-methyl-1(or 2),2,4,4a,5,6,7,8a,9-octahydropyrazolo-[3,4-g][1,4]benzoxazine A solution was prepared from 1.12 g of potassium t-butoxide in 25 ml of THF. The solution was placed under a nitrogen atmosphere and cooled to about 0°. A second solution of 0.93 g of trans-($\pm$)-4-n-propyl-7-oxo-3,4,4a,5,6,7,8,8a-octahydro-2H-[1,4]benzoxazine and 1.48 g of ethyl formate (1.6 ml) in 25 ml of THF was added rapidly in dropwise fashion with stirring. The reaction mixture was stirred at 0° C. for 15 minutes and then at ambient temperature for about 2 hours. TLC (silica gel, 1:1 THF/hexane plus trace of ammonium hydroxide) indicated that there was complete conversion of the 7-oxo compound to the 6-formyl-7-oxo derivative (it should be noted that this "formyl" product is actually four tautomers as set forth in the previous discussion of the structure of compound XX following Reaction Scheme II). 0.96 g of anhydrous hydrazine were added and the pH of the subsequent mixture adjusted to about 9 with 1N hydrochloric acid. The reaction mixture was stirred at ambient temperature for 2 hours and was then poured into 10% aqueous sodium hydroxide. The basic mixture was extracted twice with equal volumes of methylenedichloride. The methylenedichloride solutions were combined, and the combined solutions were washed with brine and then dried. Evaporation of the solvent in vacuo yielded 0.9 g of a lightly colored oil comprising trans-($\pm$)-5-n-propyl-1,4,4a,5,6,7,8a,9-octahydropyrazolo[3,4-g][1,4]benzoxazine and trans-($\pm$)-5-n-propyl-2,4,4a,5,6,7,8a,9-octahydropyrazolo[3,4-g][1,4]benzoxazine. The product was chromatographed over florisil using chloroform containing 2% methanol as the eluant. Fractions containing the desired octahydropyrazolobenzoxazine tautomers were combined, and the solvent removed from the combined fractions in vacuo to yield 530 mg of a one spot product. This product was converted to the hydrochloride salt by dissolution in 20 ml of methanol to which was added 24 ml of 0.1N hydrochloric acid. The solution was concentrated in vacuo to yield a yellow solid. The solid was dissolved in methanol, and the methanol solution decolorized. The solution was then concentrated in vacuo. The resulting residue was dissolved in boiling methanol. Ethyl acetate was added to the point of incipient precipitation. The crystallization mixture was cooled, and the resulting precipitate separated by filtration. 350 mg of the hydrochloride salt of the tautomeric mixture of trans-($\pm$)-5-n-propyl-1,4,4a,5,6,7,8a,9-octahydropyrazolo[3,4-g][1,4]benzoxazine and trans-($\pm$)-5-n-propyl-2,4,4a,5,6,7,8a,9-octahydropyrazolo[3,4-g][1,4]benzoxazine were obtained melting at 290° C. with decomposition.

Analysis. Calc.: C, 55.92; H, 7.82; N, 16.30; Cl, 13.75; Found: C, 55.65; H, 7.70; N, 16.01; Cl, 13.86.

Mass spectrum analysis of the free base gave a molecular ion at 221.

A tautomeric mixture of trans-($\pm$)-5-methyl-1,4,4a,5,6,7,8a,9-octahydropyrazolo[3,4-g][1,4]benzoxazine and trans-($\pm$)-5-methyl-2,4,4a,5,6,7,8a,9-octahydropyrazolo[3,4-g][1,4]quinoline was prepared in similar fashion from trans-($\pm$)-4-methyl-3,4,4a,5,6,7,8,8a-octahydro-2H-[1,4]-benzoxazine-7-one (2.1 g) with potassium t-butoxide (2.69 g) and ethyl formate (3.55 g) in 100 ml of THF. The formyl derivative was reacted with 2.3 g of anhydrous hydrazine to give 1.8 g of a crude product comprising trans-($\pm$)-5-methyl-1,4,4a,5,6,7,8a,9-octahydropyrazolo[3,4-g][1,4]benzoxazine and its tautomer. The crude product was purified by chromatography using the procedure set forth above for the 5-n-propyl derivative. 1.4 g of purified product were obtained. The material was one spot by TLC using the above chromatographic system. The monohydrochloride salt was prepared as above and recrystallized from methanol-ethyl acetate. The salt melted above 260° C. after a three-fold crystallization from methanol/ethyl acetate.

Analysis. Calc.: C, 52.29; H, 7.02; N, 18.29; Cl, 15.43; Found: C, 52.35; H, 7.26; N, 18.13; Cl, 15.63.

EXAMPLE 4

Preparation of Trans-($\pm$)-2-amino-6-n-propyl-5a,6,7,8,9a,10-hexahydro-5H-pyrimido[5,4-g][1,4]benzoxazine A reaction mixture was prepared from 2 g of trans-($\pm$)-4-n-propyl-3,4,4a,5,6,7,8,8a-octahydro-2H-[1,4]benzoxazine-7-one and 5 g of tris (dimethylamino)methane in 40 ml of toluene. The reaction mixture was heated at reflux temperature under nitrogen with stirring for about 2 hours. TLC (using the same system as in the previous example) indicated complete reaction of the 7-ketone to form the corresponding 6-dimethylaminomethylene-7-ketone. The volatile constituents were removed in vacuo, and the residue dissolved in 80 ml of anhydrous ethanol. About 1.98 g of guanidine carbonate were added. This new reaction mixture was heated to reflux temperature overnight with stirring under a nitrogen blanket, and was then cooled in an ice bath and filtered. The filter cake was slurried in water and refiltered to yield 900 mg of a yellow solid. The solid was dissolved in THF, and the solution was filtered. The mother liquor was concentrated to one-half of the original volume, resulting in a solid precipitate which was collected by filtration; weight=350 mg. The above filtrate was concentrated in vacuo, and the combined filtrate residue and filter cake dissolved in chloroform. The chloroform solution was washed with dilute aqueous ammonium hydroxide and then with brine. The solution was dried, and the solvent removed in vacuo to yield about 600 mg of a yellow solid. This solid was dissolved in THF, and one equivalent of 0.1N hydrochloric acid (24 ml) was added with stirring. The solvents were removed in vacuo to yield a solid residue comprising the hydrochloride salt. The residue was slurried with methanol, and the methanol evaporated. This procedure was repeated several times to remove any water which might have been present. The solid monohydrochloride salt was then recrystallized from a methanol/ethyl acetate solvent mixture to yield 300 mg of trans-($\pm$)-2-amino-6-n-propyl-5a,6,7,8,9a,10-hexahydro-5H-pyrimido[5,4-g][1,4]benzoxazine melting at 290° C. with decomposition. An additional 140 mg of product were obtained from the filtrate.

Analysis, after drying at 120° C.: Calc: C, 54.83; H, 7.43; N, 19.67; Found: C, 54.78; H, 7.30; N, 19.46.

Mass spectrum: molecular ion at 248.

EXAMPLE 5

Preparation of trans-($\pm$) 2-amino-8-n-propyl-4,4a,7,8,8a,9-hexahydro-6H-thiazolo[5,4-g][1,4]-benzoxazine A solution was prepared from 1.97 g of trans-($\pm$)-4-n-propyl-3,4,4a,5,6,7,8,8a-octahydro-2H-[1,4]-benzoxazin-7-one in 20 ml of glacial acetic acid. 2.3 ml of 38% hydrogen bromide in glacial acetic acid (freshly prepared) were added, and the resulting mixture stirred. Next, 0.4 ml of bromine in 5 ml of glacial acetic acid were added in dropwise fashion while illuminating the reaction mixture with a sun lamp. The bromine color was discharged rapidly. After all the bromine had been added, the sun lamp was removed, and the reaction mixture stirred at ambient temperature for an additional 30 minutes. The solvent was then removed in vacuo. The resulting residue was dissolved in 50 ml of anhydrous ethanol. 0.84 g of Thiourea were added, and the resulting mixture refluxed with stirring under a nitrogen blanket overnight. The reaction mixture was then cooled to room temperature, and filtered. 2.8 g of a solid were obtained which by TLC (2:1 THF/hexane plus a trace of ammonia or 9:1 chloroform/methanol plus a trace of ammonia) had one major spot. The filter cake was twice recrystallized from methanol to give 1 g of trans-($\pm$)-2-amino-8-n-propyl-4,4a,7,8,8a,9-hexahydro-6H-thiazolo[5,4-g][1,4]benzoxazine dihydrobromide melting at 297° C. with decomposition.

Analysis. Calc.: C, 34.71; H, 5.10; N, 10.12; S, 7.72; Br, 38.49; Found: C, 34.57; H, 4.95; N, 9.90; S, 7.73; Br, 38.56.

Mass spectrum of the free base obtained from the above salt gave a molecular ion at 253.

EXAMPLE 6

Preparation of α,β-Trans-($\pm$)-5-n-propyl-7-methylmercaptomethyl-2,4,4a,5,6,7,8a,9-octahydropyrazolo[4,3-g][1,4]benzoxazine and α,β-Trans-($\pm$)-5-n-propyl-7-methylmercaptomethyl-1,4,4-a,5,6,7,8a,9-octahydropyrazolo[4,3-g][1,4]benzoxazine A reaction mixture was prepared from 30.6 g of 2,4-dimethoxyaniline and 20.2 g of triethylamine in 500 ml of methylene dichloride. The solution was cooled to about 0°. 18.5 g of propionyl chloride were added with stirring under a nitrogen blanket. After the addition had been completed, the reaction mixture was allowed to warm to ambient temperature for about 1 hour. The reaction mixture was then extracted successively with equal volumes of 1N hydrochloric acid, water, saturated aqueous sodium bicarbonate solution and brine. The methylene dichloride solution was then dried, and the solvent removed in vacuo. 42 g of the crude propionylanilide were obtained as a dark oily residue. The residue was chromatographed over silica using 25% ethyl acetate in toluene as the eluant. Fractions containing the desired propionylanilide were combined, and the solvent evaporated therefrom to yield 33 g of a solid. The solid was dissolved in ethyl acetate and the solution decolorized with carbon. The carbon was separated by filtration, and the filtrate evaporated to dryness in vacuo to yield 27.8 g of N-propionyl-2,4-dimethoxyaniline melting at 63°–5° C. after recrystallization from an ethyl acetate/hexane solvent mixture; total yield of recrystallized material=67%.

A solution was prepared by dissolving 20.9 g of the above propionylanilide in 500 ml of methylenedichloride. The solution was cooled to about 0° C., and 43.9 g of aluminum chloride added thereto over a 20 minute period using an addition flask connected to the reaction vessel by rubber tubing. After the addition had been completed, the reaction mixture was stirred at ambient temperature for about 6 hours. At this time, an aliquot of the reaction mixture indicated the reaction had preceded to an extent of only about 50%. Stirring was therefore continued at ambient temperature overnight. The reaction mixture was then poured over ice, and the aqueous mixture extracted with methylenedichloride. The methylenedichloride layer was washed with brine and then dried. Evaporation of the methylenedichloride yielded a solid of N-propionyl-2-hydroxy-4-methoxyaniline; weight=17.3 g.

50 ml. of 1M BH$_3$ in THF were cooled to about 0° C. A solution of 4.88 g of the above propionylanilide in 50 ml of THF was added thereto in dropwise fashion with stirring under a nitrogen blanket. After the addition had been completed, the reaction mixture was warmed to ambient temperature and then was refluxed for about 1 hour. The reaction mixture was cooled, and 100 ml of 6N hydrochloric acid added thereto with caution. The THF was removed in vacuo, and the remaining acidic solution heated on a steam bath for about 30 minutes. The solution was cooled, and the cooled solution extracted with an equal volume of ethyl acetate. The ethyl acetate extract was discarded. The pH of the acidic aqueous layer was adjusted to about 7 by the addition of 50% aqueous sodium hydroxide. The neutral solution was extracted several times with equal volumes of methylenedichloride. The methylenedichloride extracts were combined, and the combined extracts washed with brine and then dried. Removal of the solvent in vacuo yielded 2 g of a dark colored solid, comprising N-(n-propyl)-2-hydroxy-4-methoxyaniline.

Six grams of this compound were dissolved in 200 ml of acetone to which had been added 4.83 g of potassium carbonate. A solution of 8.58 g of ethyl 2,3-dibromopropionate in 75 ml of acetone was added in dropwise fashion with stirring under a nitrogen blanket. After the addition had been completed, the reaction mixture was heated at reflux overnight while maintaining the nitrogen atmosphere. The reaction mixture was then cooled and filtered. The filtrate was concentrated to dryness in vacuo to leave a residue comprising ethyl 4-n-propyl-7-methoxy-3,4-dihydro-2H-[1,4]benzoxazinyl-2-carboxylate formed in the above reaction. 7.2 g of this residue, a dark colored oil, were combined with 2.4 g of the same product obtained in a previous reaction, and the combined fractions dissolved in ethyl acetate. The ethyl acetate solution was extracted once with an equal volume of 1N hydrochloric acid followed by extraction with an equal volume of water, an equal volume of 1N aqueous sodium hydroxide and an equal volume of brine. The ethyl acetate solution was then dried, and the solvent removed in vacuo to yield 7.8 g of an oily residue. An additional 0.6 g of material were obtained by making the above acidic extract basic with concentrated ammonium hydroxide, extracting the basic mixture with chloroform, and evaporating the chloroform. Ethyl 4-n-propyl-6-methoxy-3,4-dihydro-2H-[1,4]benzoxazinyl-2-carboxylate thus prepared distilled at about 150° C. at 0.025 torr; yield=about 57%.

Analysis. Calc.: C, 64.50; H, 7.58; N, 5.01; Found: C, 64.27; H, 7.29; N, 5.10.

A slurry was prepared from 1.52 g of lithium aluminum hydride and 50 ml of THF under a nitrogen atmosphere. A solution of 5.58 g of ethyl 4-n-propyl-7-methoxy-3,4-dihydro-2H-[1,4]benzoxazinyl-2-carboxylate in 50 ml of THF was added thereto in dropwise fashion with stirring. The addition being completed, the reaction mixture was heated to reflux temperature for about 2 hours and was then decomposed by the cautious addition of saturated aqueous ammonium chloride and water. Ether was added to break up the resulting emulsion. The mixture was filtered, and the filtrate evaporated to dryness in vacuo. The residue, containing 2-hydroxymethyl-4-n-propyl-7-methoxy-3,4-dihydro-2H-[1,4]benzoxazine formed in the above reaction, was dissolved in ethyl acetate, and the ethyl acetate solution washed with brine and then dried. Evaporation of the ethyl acetate yielded 4.6 g of an oil comprising 2-hydroxymethyl-4-n-propyl-7-methoxy-3,4-dihydro-2H-[1,4]benzoxazine. Following the procedure of Example 1, 2-hydroxymethyl-4-n-propyl-7-methoxy-3,4-dihydro-2H-[1,4]benzoxazine thus obtained was subjected to a Birch reduction. In this procedure, a solution of 0.45 g of lithium in 40 ml of anhydrous liquid ammonia was prepared. A solution of 2.37 g of the benzoxazine in 15 ml of THF was added thereto in dropwise fashion. The reaction mixture was stirred for 30 minutes at ambient temperature, at which time 10 ml of ethanol were added, and the reaction mixture allowed to warm to room temperature over a 45 minute period. 50 ml of water were added, and the aqueous mixture extracted several times with equal volumes of methylenedichloride. The methylenedichloride extracts were combined, and the combined extracts were washed with brine and then dried. Evaporation of the solvent yielded a dark colored oil comprising 2-hydroxymethyl-4-n-propyl-7-methoxy-3,4,5,8-tetrahydro-2H-[1,4]benzoxazine formed in the above reaction; yield=2.3 g. The enamine thus obtained was dissolved in 50 ml of methanol. One milliliter of glacial acetic acid was added to the methanol solution. A solution of 0.98 g of sodium borohydride in 25 ml of anhydrous ethanol was next added thereto in dropwise fashion with stirring at such a rate that the reaction temperature did not exceed about 30° C. After all the sodium borohydride solution had been added, the reaction mixture was stirred at room temperature for 1 hour. The pH was then adjusted to about 1.5 by the dropwise addition of 6N hydrochloric acid. This new reaction mixture was stirred overnight at ambient temperature and was then filtered to remove a precipitate. The filtrate was concentrated in vacuo, and the resulting residue dissolved in water. The pH of the solution was adjusted to about 11 by the addition of concentrated aqueous ammonium hydroxide. The alkaline solution was then extracted twice with an equal volume of methylenedichloride. The methylenedichloride extracts were combined, and the solution washed with brine and then dried. Removal of the solvent in vacuo yielded 1.5 g of an oil comprising a mixture of α and β-trans-(±)-2-hydroxymethyl-4-n-propyl-7-oxo-3,4,4a,5,6,7,8,8a-octahydro-2H-[1,4]benzoxazine formed in the above series of reactions. The residue was dissolved in 20 ml of methylenedichloride to which was added in dropwise fashion with stirring under a nitrogen blanket, a solution of 2.6 g of sodium bisulfite in 20 ml of water. The reaction mixture was stirred overnight at ambient temperature still under a nitrogen atmosphere. Additional water and methylenedichloride were added, and the aqueous and organic phases separated. The organic phase was extracted with water. The water extract was combined with the aqueous phase which was extracted once again with methylenedichloride. The aqueous phase was then made alkaline (pH adjusted to about 12) by the addition of 50% aqueous sodium hydroxide. The basic solution was extracted several times with equal volumes of methylenedichloride. The methylenedichloride extracts were combined, and the combined extracts washed with brine and then dried. Evaporation of the methylenedichloride in vacuo yielded 1.1 g of a lightly colored oil; molecular ion by mass spectrum at 227. NMR was consistent with the postulated structure.

A second run, starting with 11.4 g of 2-hydroxymethyl-4-n-propyl-7-methoxy-3,4-dihydro-2H-[1,4]benzoxazine yielded 4.3 g of the mixture of the α and β trans-(±) racemates weighing 4.3 g.

TLC indicated two major components which would correspond to the two diastereoisomeric pairs.

The α and β trans-(±) racemates thus prepared were separated as follows: The stereoisomeric mixture was chromatographed over florisil using 2% methanol in chloroform as the eluant. 3.09 g of product were obtained, which product was still a two-component mixture. This product was rechromatographed over florisil using 0.5% methanol in chloroform as the eluant. Some separation of the two stereoisomeric pairs occurred. 2.1 g of a first component containing minor amounts of a second component were collected. Fractions containing chiefly the second component, essentially a one spot material, were also collected. These two components, labeled isomer I and isomer II respectively, were converted via an intermediate 6-formyl derivative to the corresponding pyrazoloquinolines by the method of Example 2. First, 1.1 g of isomer I was reacted with 1.68 g of potassium t-butoxide and 1.48 g of ethyl formate in 40 ml of THF to yield an intermediate 6-formyl derivative. Next, 1.92 g of anhydrous hydrazine was added, thus forming α-trans-(±)-5-n-propyl-7-hydroxymethyl-2,4,4a,5,6,7,8a,9-octahydropyrazolo[4,3-g][1,4]benzoxazine and its tautomer, α-trans-(±)-5-n-propyl-7-hydroxymethyl-1,4,4a,5,6,7,8a,9-octahydropyrazolo[4,3-g][1,4]benzoxazine. The pyrazolobenzoxazine tautomeric mixture was isolated by the procedure of Example 2 to yield 530 mg of product. Further chromatography of this material over florisil using 2% methanol in chloroform as the eluant yielded a non-pyrazole-containing component and a fast moving impurity, both of which were discarded. Eventually, 160 mg of the desired pyrazolobenzoxazine were obtained. Prior elution had yielded a 90 mg of a second pyrazolobenzoxazine reflecting the fact that the starting material contained some isomer II, which gave the β-trans-(±) tautomer mixture on reaction with ethyl formate in the presence of base followed by reaction with anhydrous hydrazine. All fractions containing the α-trans-(±) isomer were combined and converted to the corresponding hydrochloride salt with 0.1N hydrochloric acid. The crystalline hydrochloride salt thus prepared was recrystallized from methanol/ethyl acetate to yield 60 mg of product melting 171°-3° C.; molecular ion by mass spectrum=251.

Isomer II of trans-(±)-2-hydroxymethyl-4-n-propyl-3,4,4a,5,6,7,8,8a-octahydro-2H-[1,4]benzoxazine was converted to the β-trans-(±)-5-n-propyl-7-hydroxymethyl-2,4,4a,5,6,7,8a,9-octahydropyrazolo[4,3-g][1,4]benzoxazine and its tautomer, β-trans-(±)-5-n-propyl-7-hydroxymethyl-1,4,4a,5,6,7,8a,9-octahydropyrazolo[4,3-g][1,4]benzoxazine by the above method. The pyrazolobenzoxazine was purified by chromatography over florisil using 2% methanol in chloroform as the eluant. 360 mg of a single spot material were eluted comprising the desired β-trans-(±) tautomeric mixture. The monohydrochloride salt was prepared using 1 equivalent of 1N hydrochloride acid in methanol. Removal of the solvent in vacuo, and recrystallization of the residue twice from a methanol/ethyl acetate solvent mixture yielded 180 mg of the β-trans-(±) tautomeric mixture melting at 174°-7° C.; molecular ion at 251.

The above ⊕-trans-(±)- and β-trans-(±)-racemates are converted to the corresponding 7-methanesulfonyloxymethyl (mesyloxymethyl) derivatives by reaction with methanesulfonyl chloride. The mesylate can then be reacted with the sodium salt of methylmercapton according to the procedure of Examples 5 and 6, columns 17 and 18, U.S. Pat. No. 4,199,415 to yield α-trans-(±)-5-n-propyl-7-methylthiomethyl-2,4,4a,5,6,7,8a,9-octahydropyrazolo[4,3-g][1,4]benzoxazine and its tautomer, α-trans-(±)-5-n-propyl-7-methylthiomethyl-1,4,4a,5,6,7,8a,9-octahydropyrazolo[4,3][1,4]benzoxazine or β-trans-(±)-5-n-propyl-7-methylthiomethyl-2,4,4a,5,6,7,8a,9-octahydropyrazolo[4,3-g][1,4]benzoxazine and its tautomer, β-trans-(±)-5-n-propyl-7-methylthiomethyl-1,4,4a,5,6,7,8a,9-octahydropyrazolo[4,3g][1,4]benzoxazine.

The above intermediate mesyloxymethyl derivative can be transformed into other 7-derivatives such as the methoxymethyl, cyanomethyl and the like by substituting the appropriate reagent for the sodium salt of methylmercaptane in the above synthesis. The 7-carboxamido derivatives is prepared by hydrolysis of the corresponding 7-cyano derivative.

As previously stated, the ultimate products of this invention, particularly those represented by formulas IV⇌IVa—IX above, are D-2 dopamine agonists. One of the activities attributable to a D-2 dopamine agonist is the inhibition of prolactin secretion, as demonstrated by the following procedure.

Adult male rats of the Sprague-Dawley strain weighing about 200 g. were housed in an air-conditioned room with controlled lighting (lights on 6 a.m.-8 p.m.) and fed lab chow and water ad libitum. Each rat received an intraperitoneal injection of 2.0 mg. of reserpine in aqueous suspension 18 hours before administration of the test drug. The purpose of the reserpine was to keep the rat prolactin levels uniformly elevated. The test compound was dissolved in 10 percent ethanol, and the ethanol solution injected intraperitoneally at doses of 0.017, 0.03, 0.17 and 0.3µ moles/kg. The drug was administered at each of several dose levels to groups of 10 rats, and a control group of 10 intact males received an equivalent amount of 10 percent ethanol. One hour after treatment, all rats were killed by decapitation, and 150 µl aliquots of serum were assayed for prolactin.

The difference between the prolactin level of the treated rats and prolactin level of the control rats, divided by the prolactin level of the control rats, gives the percent inhibition of prolactin secretion attributable to the given dose of the drug under test. Such inhibition percentages are given in Table 1 below for drugs of this invention. In Table 1, column 1 gives the name of the compound, column 2, the dose level in mg/kg and column 3, the % inhibition of serum prolactin.

TABLE 1

| Name of Compound | dose mg/kg | % inhibition |
|---|---|---|
| trans-(±)-5-methyl-2,4,4a,5,6,7,8a,9-octahydropyrazolo[4,3-g][1,4]benzoxazine.HCl | 50 | 37 |
| trans-(±2-amino-6-n-propyl-5a,6,7,8,9a,10-hexahydro-5H—pyrimido[5,4-g][1,4]-benzoxazine.HCl | 50 | 70 |
| trans-(±)-5-n-propyl-2,4,4a,5,6,7,8a,9-octahydropyrazolo[3,4-g][1,4]benzoxazine.HCl | 500 | 92 |
|  | 100 | 35 |
|  | 10 | stimulated |
| trans-(±)-2-amino-8-n-propyl-4,4a,7,8,8a,9-hexahydro-6H—thiazolo[5,4-g][1,4]benzoxazine.diHBr | 50 | 51 |

The compounds of this invention are administered for therapeutic purposes in a variety of oral formulations as illustrated below.

Hard gelatin capsules are prepared using the following ingredients:

|  | Quantity (mg./capsule) |
|---|---|
| Active compound | .5–10 mg |
| Starch dried | 200 |
| Magnesium stearate | 10 |

The above ingredients are mixed and filled into hard gelatin capsules.

A tablet formulation is prepared using the ingredients below:

|  | Quantity (mg./tablet) |
|---|---|
| Active compound | .5–10 mg |
| Cellulose, microcrystalline | 400 |
| Silicon dioxide, fumed | 10 |
| Stearic acid | 5 |

The components are blended and compressed to form tablets.

Alternatively, tablets each containing 0.5–10 mg of active ingredient are made up as follows:

| Active ingredient | .5–10 mg. |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets.

Capsules each containing 0.5–10 mg of medicament are made as follows:

| Active ingredient | .5–10 mg |
|---|---|
| Starch | 59 mg |
| Microcrystalline cellulose | 59 mg |
| Magnesium stearate | 2 mg |

The active ingredient, cellulose, starch and magnesium stearate are blended, passed through a No. 45 mesh U.S. sieve, and filled into hard gelatin capsules.

Suspensions each containing 0.5–10 mg. of medicament per 5 ml dose are made as follows:

| Active ingredient | .5–10 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

For oral administration, tablets, capsules or suspensions containing from about 0.05 to about 10 mg of active drug per dose are given 3–4 times a day, giving a daily dosage of 1.5 to 40 mgs.

We claim:

1. A trans-(±) racemate of the formula

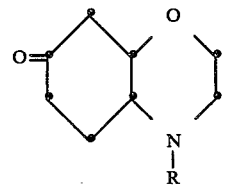

wherein R is methyl, ethyl or n-propyl.

2. An enantiomer of a racemate according to claim 1.

3. A 4aR,8aR enantiomer of a racemate according to claim 1.

4. A compound according to claim 1, said compound being trans-(±)-4-n-propyl-7-oxo-3,4,4a,5,6,7,8,8a-octahydro-2H-[1,4]benzoxazine.

5. α and β trans-(±) racemates or individual enantiomers of the formula

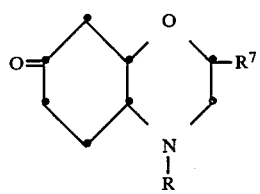

where R is methyl, ethyl and n-propyl and $R^7$ is $CH_2OH$, or $CH_2X$ wherein X is a leaving group subject to nucleophilic substitution.

6. An α and β trans-(±)-racemate or an individual enantiomer thereof according to claim 5 in which $R^7$ is $CH_2OH$.

7. α or β racemate according to claim 5 in which R is n-propyl.

8. An α and β trans-(±) racemate or an enantiomer thereof according to claim 5 in which $R^7$ is $CH_2X$.

9. An α or β trans-(±) racemate according to claim 8 in which R is n-propyl.

10. An α or β trans-(±) racemate according to claim 6 in which X is $C_{1-3}$ alkylsulfonyloxy, phenylsulfonyloxy, tolylsulfonyloxy, chlorophenylsulfonyloxy, Cl or Br.

11. An α or β trans-(±) racemate or an enantiomer thereof of the formula

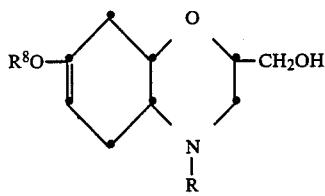

in which R and $R^8$ are individually methyl, ethyl or n-propyl.

12. An α or β trans-(±) racemate according to claim 11 in which $R^8$ is methyl.

13. An α or β trans-(±) racemate according to claim 11 in which R is n-propyl.

14. A racemate of the formula

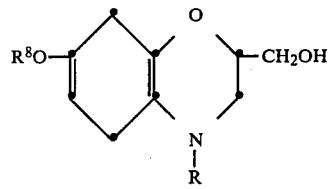

wherein each R and $R^8$ are individually methyl, ethyl or n-propyl.

15. A compound according to claim 14, said compound being 2-hydroxymethyl-4-n-propyl-7-methoxy-3,4,5,8-tetrahydro-2H-[1,4]benzoxazine.

16. A trans-(±) racemate of the formula

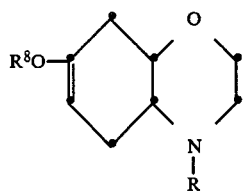

wherein R and $R^8$ are individually methyl, ethyl or n-propyl.

17. An enantiomer of a racemate according to claim 16.

18. A 4aR,8aR enantiomer of a racemate according to claim 16.

19. A compound of the formula

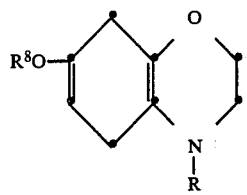

wherein R and $R^8$ are individually methyl, ethyl or n-propyl.

* * * * *